US007317526B2

(12) United States Patent
Voigt et al.

(10) Patent No.: US 7,317,526 B2
(45) Date of Patent: Jan. 8, 2008

(54) SYSTEM AND METHOD FOR DYNAMIC CHEMICAL IMAGING

(75) Inventors: Thomas C. Voigt, Export, PA (US); David Tuschel, Monroeville, PA (US); John S. Maier, Pittsburgh, PA (US)

(73) Assignee: Chem Image Corporation, Pittsburgh, PA (US)

(*) Notice: Subject to any disclaimer, the term of this patent is extended or adjusted under 35 U.S.C. 154(b) by 77 days.

(21) Appl. No.: 11/399,032

(22) Filed: Apr. 6, 2006

(65) Prior Publication Data

US 2006/0268267 A1 Nov. 30, 2006

Related U.S. Application Data

(63) Continuation of application No. 10/882,082, filed on Jun. 30, 2004, now Pat. No. 7,046,359.

(51) Int. Cl.
*G01J 3/44* (2006.01)
*G01N 21/65* (2006.01)

(52) U.S. Cl. ........................................ 356/301

(58) Field of Classification Search ................ 356/301
See application file for complete search history.

(56) References Cited

U.S. PATENT DOCUMENTS 5,377,003 A 12/1994 Lewis et al.
5,528,393 A 6/1996 Sharp et al.

(Continued)

FOREIGN PATENT DOCUMENTS

WO PCT/CA98/00092 8/1998

OTHER PUBLICATIONS

Treado et al., "Indium Antimonide (InSb) Focal Plane Array(FPA) Detection for Near-Infrared Imaging Microscopy," Applied Spectroscopy 48 (1994) p. 607.

(Continued)

*Primary Examiner*—F. L. Evans
(74) *Attorney, Agent, or Firm*—Morgan, Lewis & Bockius LLP

(57) ABSTRACT

A system and method for detecting dynamic changes that occur in a sample between a first time interval and a second time interval using a series of at least first and second sequential chemical images of the sample. During the first time interval: (i) the sample is illuminated with a plurality of photons to thereby produce photons scattered or emitted by the sample; (ii) a two-dimensional array of detection elements is used to simultaneously detect scattered or emitted photons in a first predetermined wavelength band from different locations on or within the sample; and (iii) the two-dimensional array of detection elements is thereafter used one or more further times to simultaneously detect scattered or emitted photons in one or more further predetermined wavelength band(s) from different locations on or within the sample. The outputs of the two-dimensional array of detection elements during the first time interval are then combined to generate the first chemical image of the sample. The process is repeated during the second time interval to generate the second chemical image of the sample. Dynamic changes occurring in the sample between the first time interval and the second time interval are detected based on one or more differences between the first and second chemical images.

2 Claims, 2 Drawing Sheets

U.S. PATENT DOCUMENTS

| | | | |
|---|---|---|---|
| 5,626,134 | A | 5/1997 | Zuckerman |
| 5,784,162 | A | 7/1998 | Cabib et al. |
| 5,866,430 | A | 2/1999 | Grow |
| 5,910,816 | A | 6/1999 | Fontenot et al. |
| 6,002,476 | A | 12/1999 | Treado |
| 6,052,187 | A | 4/2000 | Krishnan et al. |
| 6,069,690 | A | 5/2000 | Xu et al. |
| 6,175,750 | B1 | 1/2001 | Cook et al. |
| 6,181,414 | B1 | 1/2001 | Raz et al. |
| 6,274,871 | B1 | 8/2001 | Dukor et al. |
| 6,300,618 | B1 | 10/2001 | Tanaami et al. |
| 6,483,641 | B1 | 11/2002 | MacAulay |
| 6,485,413 | B1 | 11/2002 | Boppart et al. |
| 6,640,130 | B1 | 10/2003 | Freeman et al. |
| 6,640,132 | B1 | 10/2003 | Freeman et al. |
| 6,697,665 | B1 | 2/2004 | Rava et al. |
| 6,741,884 | B1 | 5/2004 | Freeman et al. |
| 6,810,279 | B2 | 10/2004 | Mansfield et al. |
| 6,937,885 | B1 | 8/2005 | Lewis et al. |
| 6,939,686 | B2 | 9/2005 | Ling et al. |

OTHER PUBLICATIONS

Morris, Hoyt, Miller and Treado, "Liquid Crystal Tunable Filter Raman Chemical Imaging," Applied Spectroscopy, No. 50, No. 6, (Jun. 1996) pp. 805-811.

Patrick J. Treado, "Chemical Imaging Reveals More Than The Microscope," Laser Focus World, (Oct. 1995) pp. 1-7.

Morris, "Utrasensitive Raman and Flourescence Imaging Using Liquid Crystal Tunable Filters," SPIE vol. 2385, (1995) pp. 81-87.

Treado et al., "Infrared Raman Spectroscopic Imaging," (Marcell Decker, 1992) pp. 71-108.

Treado et al., "High-Fidelity Raman Imaging Spectrometry: A Raid Method Using an Acousto-Optic Tunable Filter", Applied Spectroscopy, vol. 46, No. 8 (1992) pp. 1211-1216.

Treado et al., "Near-Infrared Acousto-Optic Filtered Spectoscopic Microscopy: A Solid-State Approach to Chemical Imaging," Applied Spectroscopy, vol. 46, No. 4 (1992) pp. 553-559.

Morris et al., "Imaging Spectometers for Fluorescence and Raman Microscopy: Acousto-Optic and Liquid Crystal Tunable Filter," Applied Spectroscopy, vol. 48, No. 7, (1994) pp. 857-860.

Turner et al., "LCTF Raman Chemical Imaging in the Near-Infrared," SPIE vol. 3061 (1997) pp. 280-283.

Miller et al., "Multispectral Imaging with a Liquid Crystal Tunable Filter," SPIE vol. 2345, (1995) pp. 354-365.

Ling et al., "Direct Raman Imaging Techniques for Study of the Subcellular Distribution of a Drug," Applied Optics, vol. 41, No. 28, (2002) pp. 6000-6017.

200
Image Sensor
145
Laser
110
LCTF
140
Laser Rejection Filter
112
Mirror
115
135
120
Lens
100
105
130
Mirror
118
125
116
Lens
114
XYZ Sample Position Stage Image Sensor
145
200
LCTF
140
Laser Rejection Filter
135
Mirror
130
118
116
Lens
125
100
XYZ Sample Position Stage
105
114
Laser
110
112
Mirror
115
Lens
120

SYSTEM AND METHOD FOR DYNAMIC CHEMICAL IMAGING

RELATED APPLICATIONS

This application is a continuation of U.S. application Ser. No. 10/882,082 filed Jun. 30, 2004 now U.S. Pat. No. 7,046,359. The present application is related to U.S. patent application Ser. No. 10/879,636 filed Jun. 30, 2004 incorporated herein by reference in its entirety. Each of the above-referenced applications is assigned to the assignee of the present application.

FIELD OF THE INVENTION

The present invention relates generally to chemical imaging and, in particular, to the use of chemical imaging to detect dynamic changes in a sample.

BACKGROUND

Chemical imaging is known in the art. One example of an apparatus used for chemical imaging is taught in U.S. Pat. No. 6,002,476, entitled "Chemical Imaging System," to Treado et al. Among other things, U.S. Pat. No. 6,002,476 teaches the use of Raman chemical imaging for analysis of a static sample, e.g., for assessing whether a particular tissue sample corresponds to normal tissue or breast cancer tissue. Other chemical imaging systems for assessment of static samples exist in the art.

In contrast to the prior art, the present invention uses chemical imaging to assess and observe non-static samples (i.e., samples that vary over time). Among other things, the present invention may be used to detect dynamic changes that occur in the sample over an observation period.

SUMMARY OF THE INVENTION

The present invention is directed to a system and method for detecting dynamic changes that occur in a sample between a first time interval and a second time interval using a series of at least first and second sequential chemical images of the sample, wherein the first chemical image corresponds to an image of the sample during a first time interval, and the second chemical image corresponds to an image of the sample at a second time interval after the first time interval. During the first time interval: (i) the sample is illuminated with a plurality of photons to thereby produce photons scattered or emitted by the sample; (ii) a two-dimensional array of detection elements is then used to simultaneously detect scattered or emitted photons in a first predetermined wavelength band from different locations on or within the sample; and (iii) the two-dimensional array of detection elements is thereafter used one or more further times to simultaneously detect scattered or emitted photons in one or more further predetermined wavelength band(s) from different locations on or within the sample. The outputs of the two-dimensional array of detection elements during the first time interval are then combined to generate the first chemical image of the sample.

During the second time interval: (i) the sample is illuminated with a plurality of photons to thereby produce photons scattered or emitted by the sample; (ii) the two-dimensional array of detection elements is then used to simultaneously detect scattered or emitted photons in a first predetermined wavelength band from different locations on or within the sample; and (iii) the two-dimensional array of detection elements is thereafter used one or more further times to simultaneously detect scattered or emitted photons in one or more further predetermined wavelength band(s) from different locations on or within the sample. The outputs of the two-dimensional array of detection elements during the second time interval are then combined to generate the second chemical image of the sample.

Dynamic changes occurring in the sample between the first time interval and the second time interval are next detected based on one or more differences between the first and second chemical images.

The present invention permits rapid observation of the sample with full spatial information, and allows the monitoring of the evolution and changes in the sample that are naturally proceeding or occurring (i.e., under equilibrium conditions,) as well as those that are additionally forced or imposed by creating a non-equilibrium condition via an external means (e.g., one or more external fields or forces applied to the sample). In certain embodiments, the external means may be applied to a specific location within the sample (rather than the whole sample).

DETAILED DESCRIPTION OF THE PREFERRED EMBODIMENT

Figure 1:
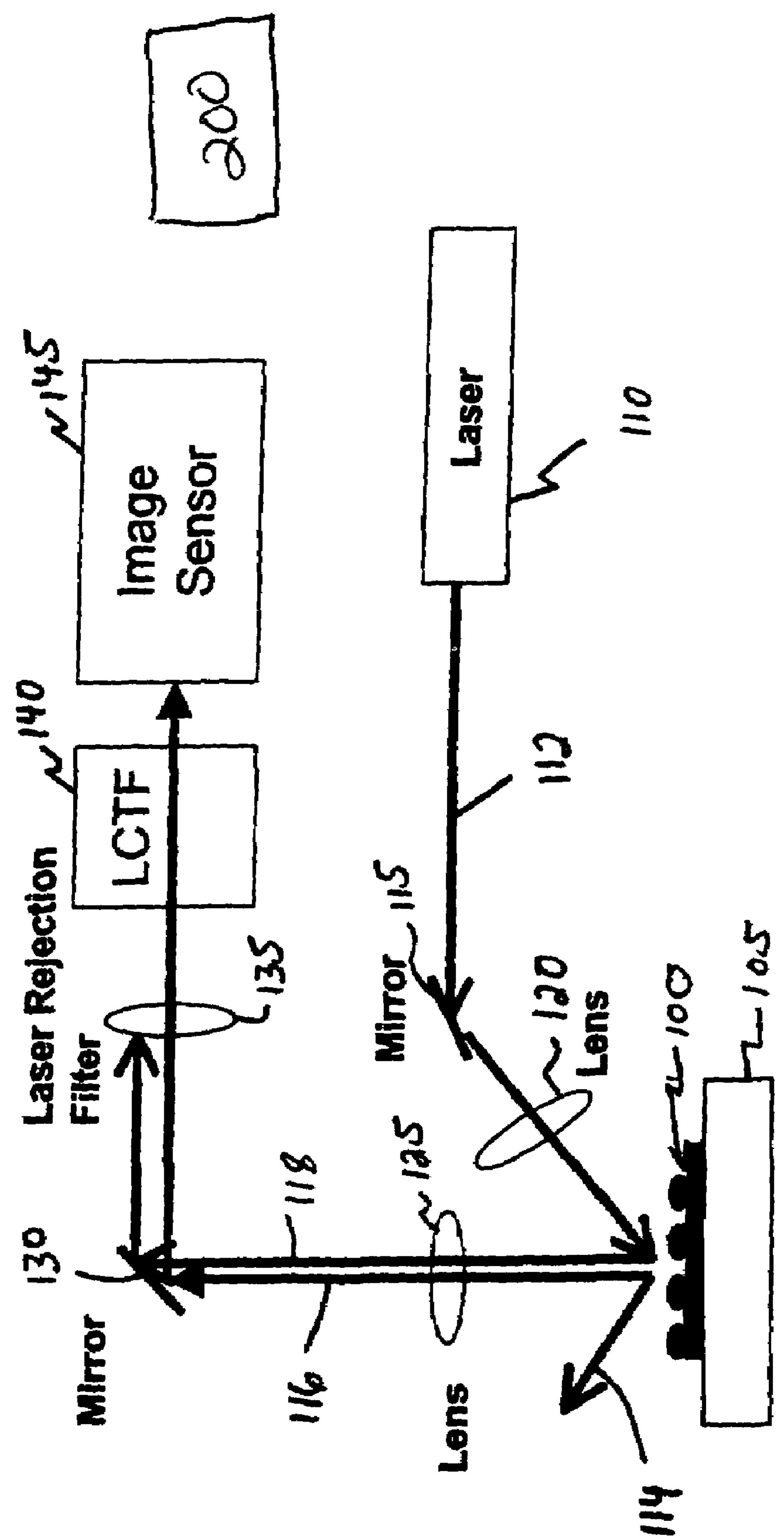
FIG. 1 schematically represents an apparatus according to one embodiment of the disclosure.

FIG. 1 schematically represents an apparatus according to one embodiment of the disclosure. The apparatus of FIG. 1 enables providing a high optical throughput for imaging low light levels at variable magnification. Referring to FIG. 1, sample 100 is positioned on substrate 105. Substrate 105 can be any conventional microscopic slide or other means for receiving and optionally securing sample 100. Light source 110 is positioned to provide incident light to sample 100. Light source 110 can include any conventional photon source, including laser, LED, and other IR or near IR devices. Light source 110 may also be selected to provide evanescence illumination of the sample. In one embodiment, the line width of the monochromatic light source is in the range of about 15-25 $cm^{-1}$.

Referring still to FIG. 1, it should be noted that light source 110 is positioned to provide incident light at an angle to sample 100 as opposed to light shining orthogonal to sample 100. In other words, the radiation used to illuminate the sample need not pass through the optical train of a conventional microscope (or macroscope); rather, it can illuminate the sample at an oblique angle from above or below sample 100. Photon beam 112 is received and deflected by mirror 115 through lens 120. Lens 120 may optionally be used to focus the light on sample 100. Alternatively, the photon beam 112 may be directed towards the sample 100 without the need for the mirror 115.

The multitude of photons in beam 112 reaching sample 100 illuminate the sample and are either scattered or absorbed by the sample, which can result in subsequent emission (luminescence) at different wavelengths. As known to those skilled in the art, the term "luminescence" includes a wide range of optical processes described using other names. These include: fluorescence, phosporescence, photoluminescence, electroluminescence, chemiluminescence, sonoluminescence, thermoluminescence and even upconversion. Scattered photons are schematically represented as beams 116 and 118 while specularly reflected photons are represented schematically as beam 114. Luminescence emitted photons are also represented as beam 118. Optical lens 125 is positioned to receive photon beams 116 and 118. Optical lens 125 may be used for gathering and focusing received photon beams. This includes gathering and focusing both polarized and the un-polarized photons. In general, the sample size determines the choice of light gathering optical lens 125. For example, a microscope lens may be employed for analysis of the sub-micron to micrometer specimens. For larger samples, macro lenses can be used. Optical lens 125 (as well as lens 120) may include a simple reduced resolution/aberration lens with a larger numerical aperture to thereby increase system's optical throughput and efficiency. Mirror 130 is positioned to direct emitted or scattered photon beams 118 to tunable filter 140. It should be noted that placement of mirror 130 is optional and may be unnecessary in configurations where tunable filter is positioned above sample 100.

Laser rejection filter 135 may be positioned prior to tunable filter 140 to filter out scattered illumination light represented by beam 116 and to optimize the performance of the system. In other words, rejection filter 135 enables spectrally filtering of the photons at the illuminating wavelength.

A conventional tunable filter (including electro-optical tunable filters) including an liquid crystal tunable filter ("LCTF") or acousto-optical tunable filter ("AOTF") can be used to further the principles of the disclosure. The electro-optical filters (interchangeably, tunable filters) allow specific wavelengths or ranges of wavelengths of light to pass through as an image, depending on the control signals placed on the device by a controller (not shown). The wavelengths that can be passed through tunable filter 140 may range from 200 nm (ultraviolet) to 2000 nm (i.e., the far infrared). The choice of wavelength depends on the desired optical region and/or the nature of the sample being analyzed.

Image sensor 145 may be a digital device such as for example a two-dimensional, image focal plane array ("FPA") or CCD or CMOS sensor. The optical region employed to characterize the sample of interest governs the choice of FPA detector. For example, a two-dimensional array of silicon charge-coupled device ("CCD") detection elements, can be employed with visible wavelength fluorescence and Raman spectroscopic, while gallium arsenide (GaAs) and gallium indium arsenide (GaInAs) FPA detectors can be employed for image analyses at near infrared wavelengths. The choice of such devices depends on the type of sample being analyzed. In one embodiment, each detection element in the two-dimensional array of detection elements used to form image sensor 145 functions to detect photons scattered or emitted from a different spatial location on or within the sample. In one embodiment, image sensor 145 produces digital images of the entire view of the sample as processed by tunable filter 140.

Figure 2:
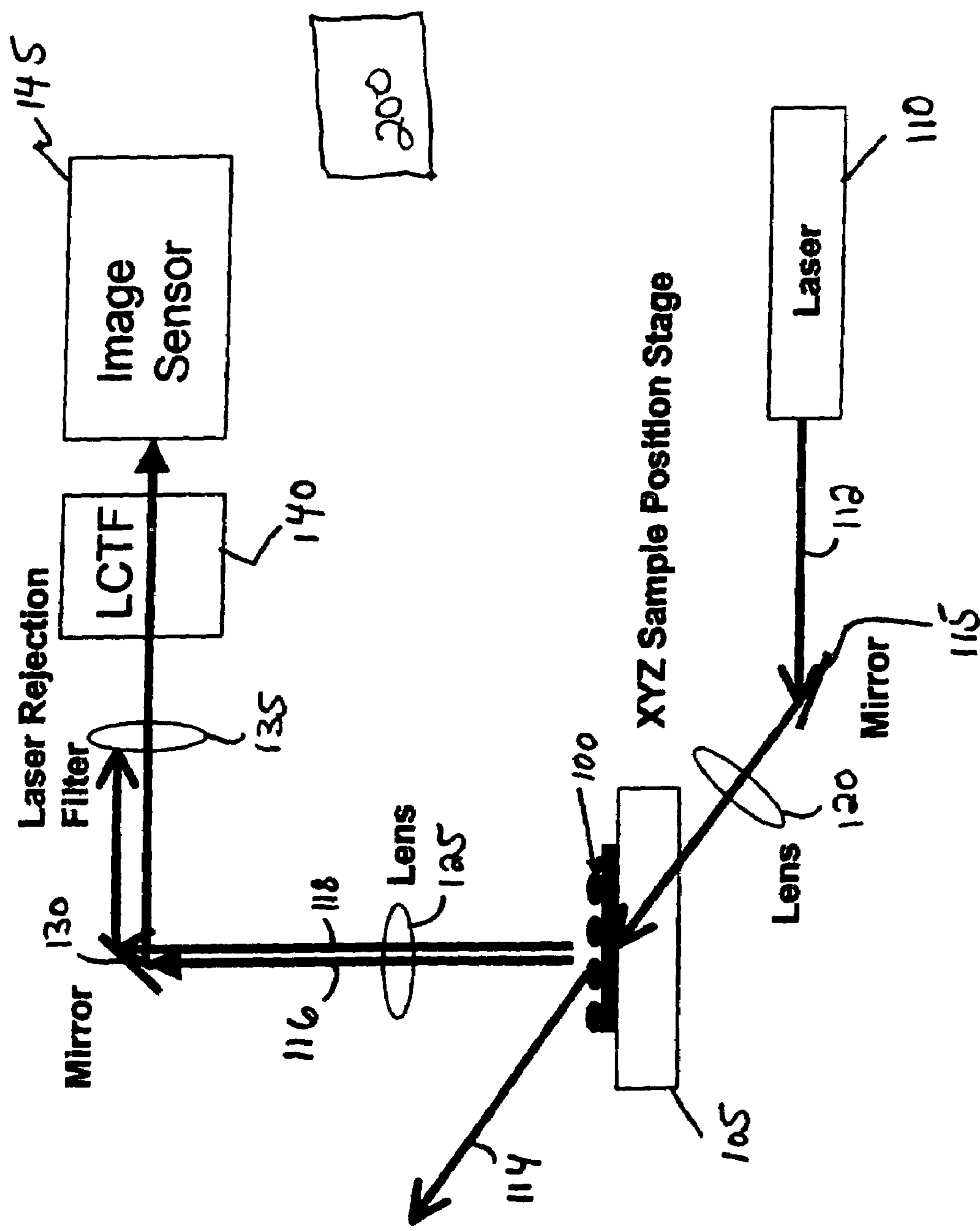
FIG. 2 schematically represent an apparatus according to another embodiment of the disclosure.

FIG. 2 schematically represents an apparatus according to another embodiment of the disclosure. More specifically, FIG. 2 schematically shows a high optical throughput configuration for imaging low light levels at variable magnification. The collection optics are similar to that illustrated in FIG. 1 but with illumination from the underside of sample 100.

It is noted that in both FIGS. 1 and 2, sample 100 is illuminated at an oblique angle. Specifically referring to FIG. 2, photonic beam 120 and the plane axis of sample 100 define an oblique angle. It has been found that through oblique illumination, a so-called "Dark Field Raman Imaging" is developed. As opposed to the conventional bright field Raman configuration, the dark field Raman imaging decouples the image capture optics from the deliver of exciting radiation. Consequently, internal scattering and attenuation of the incident radiation has been minimized to improve the signal to noise ratio. Also, the location of the optical source external to the optical train further allows the use of a lower cost, less powerful illumination source as well as enables a simpler, less expensive integration of several illumination sources into the system. The application of this configuration is not limited to Raman and luminescence imaging and can be successfully used, for example, with conventional spectroscopy.

In each of the embodiments shown in FIGS. 1 and 2, a computer or processor (200) is coupled to and used to control the optical devices including light source (110), lenses (120, 125, 135), mirrors (115, 130) and tunable filter (140). The computer is also coupled to image sensor 145 and functions to generate "chemical images" from the output of the image sensor 145. In one embodiment, each chemical image is a spatially accurate wavelength-resolved image of the sample that is formed from multiple "frames"; wherein each frame has plural spatial dimensions and is created from photons of a particular wavelength (or wave number) or from photons in a particular wavelength band (or wave number band) that are collected simultaneously by image sensor 145 from different spatial locations on or within sample 100. In each chemical image, multiple frames may be combined to form a complete image across all wavelengths (wave numbers) of interest. The chemical images generated by the computer may be further analyzed by the computer and/or displayed to a user.

The present invention uses an apparatus such as those shown in FIGS. 1 and 2 to detect dynamic changes that occur in sample 100 between a first time interval and a second subsequent time interval using a series of at least first and second sequential chemical images of sample 100. During the first time interval: (i) sample 100 is illuminated with photons from source 110 to thereby produce photons scattered or emitted by sample 100; (ii) image sensor 145 is then used to simultaneously detect scattered or emitted photons in a first predetermined wavelength band (selected by tunable filter 140) from different locations on or within the sample; and (iii) for each of one or more further predetermined wavelength band(s) (each of which is sequentially selected using tunable filter 140), image sensor 145 is thereafter used to simultaneously detect scattered or emitted photons from different locations on or within the sample. The outputs of detector 145 (for each of the wavelengths or wavelength bands selected by tunable filter 140 during the first time interval) are then combined by the computer (not shown) to generate the first chemical image of the sample.

During the second subsequent time interval: (i) sample 100 is illuminated with photons from source 110 to thereby produce photons scattered or emitted by sample 100; (ii) image sensor 145 is then used to simultaneously detect scattered or emitted photons in a first predetermined wavelength band (selected by tunable filter 140) from different locations on or within the sample; and (iii) for each of one or more further predetermined wavelength band(s) (each of which is sequentially selected using tunable filter 140), image sensor 145 is thereafter used to simultaneously detect scattered or emitted photons from different locations on or within the sample. The outputs of detector 145 (for each of the wavelengths or wavelength bands selected by tunable filter 140 during the first time interval) are then combined by the computer (not shown) to generate the second chemical image of the sample.

Dynamic changes occurring in the sample between the first time interval and the second time interval are next detected based on one or more differences between the first and second chemical images. Computer analysis of the chemical image with or without the physical image may be used to detect (or enhance detection of) the dynamic changes. The dynamic changes may also be detected by a user viewing a display of the chemical images.

In various embodiments, a series of many sequential chemical images are obtained rapidly in succession to generate a "movie" of the sample. For example, as many as 100 chemical images per second of the sample may be obtained in order to detect dynamic changes in the sample in substantially real-time. In some embodiments, the temporal resolution of the chemical images in the sequence may be as fine a 1 millisecond, i.e., the system will generate a chemical image of the sample every millisecond. Other temporal resolutions can also be selected including, for example, a temporal resolution that equates to chemical images spaced apart by as much as 15 minutes between adjacent images. When using the present invention to monitor a particular process or reaction, the temporal resolution selected should be sufficient to detect dynamic changes of interest that occur in the sample over time.

The present invention thus permits rapid observation of sample 100 with full spatial information, and allows the monitoring of the evolution and changes in sample 100 that are natural proceeding or occurring (i.e., under equilibrium conditions), as well as those that are additionally forced or imposed by creating a non-equilibrium condition via an external means (e.g., one or more external fields or forces applied to the sample). In certain embodiments, the external means are applied to a specific location within sample 100 (rather than the whole sample). Examples of samples that may be analyzed and observed used the dynamic chemical imaging techniques of the present invention includes biological samples or micro-fluidic circuits undergoing changes over time. These changes may include displacement, chemical interaction, a change in chemical state, phase change, growth, shrinkage, chemical decomposition, chemical metabolization and physical strain. Numerous other examples of samples/changes applicable to the present invention will be recognized by those skilled in the art and are considered within the scope of the present invention.

As noted above, the present invention may be used to detect dynamic changes in the sample that result from application of an external condition to the sample. Such external conditions include, for example, varying an electric or magnetic field applied to or within sample 100 between the first and second time intervals; varying an external optical field applied to or within the sample between the first and second time intervals, wherein the external optical field is distinct from the optical field initially used to illuminate the sample; varying the optical field applied to or within the sample between the first and second time intervals, wherein the additional optical field is produced by pulsing the optical filed used to illuminate the sample; varying internally generated photons applied to or within the sample between the first and second time intervals; varying a polarization used to illuminate the sample between the first and second time intervals; varying a temperature of the sample between the first and second time intervals; varying a pressure applied to the sample between the first and second time intervals; or varying a stress applied to or within the sample between the first and second time intervals. In other embodiments, a chemical gradient associated with the sample (e.g., a chemical gradient imposed on the sample) varies between the first and second time intervals. In still further embodiments, a physiological or biological stress is induced in the sample between the first and second time intervals.

In some embodiments, each chemical image in the sequence is made up of multiple separate spatially accurate wavelength-resolved images of the sample (each of which is formed from multiple "frames" as discussed above), wherein each of the multiple separate spatially accurate wavelength-resolved images corresponds to one of a plurality of different depths within the sample. These embodiments are useful for detecting chemical changes occurring throughout the volume of sample 100, rather than changes occurring on a single surface or plane of the sample.

In still further embodiments, differences between or among various chemical images in the sequence may be correlated (using, e.g., the computer discussed above or by a user) with orthogonal measurements of the sample made during each of the time intervals associated with the sequence, in order to enhance detection or observation of dynamic changes in the sample. Examples of orthogonal measurements that may be used include measurements made using the following modalities: Raman scattering, near infrared absorption (NIR), visual imagery, video or luminescence. Other orthogonal measurements may also be used and are considered to be within the scope of the present invention.

Finally, it will be appreciated by those skilled in the art that changes could be made to the embodiments described above without departing from the broad inventive concept thereof. It is understood, therefore, that this invention is not limited to the particular embodiments disclosed, but is intended to cover modifications within the spirit and scope of the present invention as defined in the appended claims.

What is claimed is:

1. A system for detecting dynamic changes that occur in a sample between a first time interval and a second time interval using a series of at least first and second sequential chemical images of the sample, wherein the first chemical image corresponds to an image of the sample during a first time interval, and the second chemical image corresponds to an image of the sample at a second time interval after the first time interval, comprising:

(a) a source that illuminates the sample with a plurality of photons to thereby produce Raman photons scattered from the sample;

(b) a two-dimensional array of detection elements that, during the first time interval, (i) simultaneously detects the Raman photons in a first predetermined wavelength band scattered from different locations on or within the sample, and (ii) thereafter, for each of a plurality of further different predetermined wavelength bands, simultaneously detects Raman photons scattered from different locations on or within the sample, wherein the two-dimensional array of detection elements generates first outputs in response to the Raman photons detected in the first predetermined wavelength band and the plurality of further predetermined wavelength bands during the first time interval;

(c) a tunable filter that, during the first time interval, allows the Raman scattered photons in the first predetermined wavelength band and the plurality of further predetermined wavelength bands to pass from different locations on or within the sample to the two-dimensional array of detection elements based on control signals generated by a processor;

(d) wherein the processor combines the first outputs of the two-dimensional array of detection elements to generate the first chemical image of the sample;

(e) wherein, during the second time interval, the two-dimensional array of detection elements, (i) simultaneously detects Raman photons, in the first predetermined wavelength band scattered from different locations on or within the sample, and (ii) thereafter, for each of the plurality of further different predetermined wavelength bands, simultaneously detects Raman photons scattered from different locations on or within the sample, wherein the two-dimensional array of detection elements generates second outputs in response to the Raman photons detected in the first predetermined wavelength band and the plurality of further predetermined wavelength bands during the second time interval;

(f) wherein, during the second time interval, the tunable filter allows the Raman photons in the first predetermined wavelength band and the plurality of further predetermined wavelength bands to pass from different locations on or within the sample to the two-dimensional array of detection elements based on control signals generated by the processor;

(g) wherein the processor combines the second outputs of the two-dimensional array of detection elements to generate the second chemical image of the sample; and (h) wherein the processor detects dynamic changes occurring in the sample between the first time interval and the second time interval based on one or more differences between the first and second chemical images.

2. A system for detecting dynamic changes that occur in a sample between a first time interval and a second time interval using a series of at least first and second sequential chemical images of the sample, wherein the first chemical image corresponds to an image of the sample during a first time interval, and the second chemical image corresponds to an image of the sample at a second time interval after the first time interval, comprising:

(a) a source that illuminates the sample, along a first optical path, with a plurality of photons to thereby produce ones of photons scattered or emitted by the sample along a second optical path, wherein the first optical path is at an oblique angle with respect to the second optical path;

(b) a two-dimensional array of detection elements that, during the first time interval, (i) simultaneously detects ones of the photons scattered or emitted, in a first predetermined wavelength band from different locations on or within the sample, and (ii) thereafter, for each of a plurality of further different predetermined wavelength bands, simultaneously detects ones of the photons scattered or emitted from different locations on or within the sample, wherein the two-dimensional array of detection elements generates first outputs in response the photons detected in the first predetermined wavelength band and the plurality of further predetermined wavelength bands during the first time interval;

(c) a tunable filter that, during the first time interval, allows ones of the photons scattered or emitted in the first predetermined wavelength band and the plurality of further predetermined wavelength bands to pass from different locations on or within the sample to the two-dimensional array of detection elements based on control signals generated by a processor;

(d) wherein the processor combines the first outputs of the two-dimensional array of detection elements to generate the first chemical image of the sample;

(e) wherein, during the second time interval, the two-dimensional array of detection elements (i) simultaneously detects ones of the photons scattered or emitted in the first predetermined wavelength band from different locations on or within the sample, and (ii) thereafter, for each of the plurality of further different predetermined wavelength bands, simultaneously detects ones of the photons scattered or emitted from different locations on or within the sample, wherein the two-dimensional array of detection elements generates second outputs in response to photons detected in the first predetermined wavelength band and the plurality of further predetermined wavelength bands during the second time interval;

(f) wherein during the second time interval, the tunable filter allows ones of the photons scattered or emitted in the first predetermined wavelength band and the plurality of further predetermined wavelength bands to pass from different locations on or within the sample to the two-dimensional array of detection elements based on control signals generated by the processor;

(g) wherein the processor combines the second outputs of the two-dimensional array of detection elements to generate the second chemical image of the sample; and (h) wherein the processor detects dynamic changes occurring in the sample between the first time interval and the second time interval based on one or more differences between the first and second chemical images.

* * * * *